(12) United States Patent
Canary et al.

(10) Patent No.: US 7,589,209 B2
(45) Date of Patent: Sep. 15, 2009

(54) 8-HYDROXYQUINOLINE TRIPODAL METAL ION PROBES

(75) Inventors: James W. Canary, New York, NY (US); Maksim Royzen, Brooklyn, NY (US)

(73) Assignee: New York University, New York, NY (US)

( * ) Notice: Subject to any disclaimer, the term of this patent is extended or adjusted under 35 U.S.C. 154(b) by 463 days.

(21) Appl. No.: 11/086,987

(22) Filed: Mar. 23, 2005

(65) Prior Publication Data

US 2005/0227365 A1    Oct. 13, 2005

Related U.S. Application Data

(60) Provisional application No. 60/555,399, filed on Mar. 23, 2004.

(51) Int. Cl.
*C07D 215/38* (2006.01)
(52) U.S. Cl. ........................ 546/159; 546/153
(58) Field of Classification Search ............... 546/153, 546/159
See application file for complete search history.

(56) References Cited

U.S. PATENT DOCUMENTS 6,277,841 B1 *    8/2001   Rajagopalan et al. ....... 514/185
6,720,188 B2 *    4/2004   Kaddurah-Daouk et al. .. 436/86

OTHER PUBLICATIONS

Best, ChemBioChem, vol. 5(6), pp. 811-819, 2004.*
Bronson, Tetrahedron, vol. 60(49), pp. 11139-11144, 2004.*
Serratrice, Inorgtanic Chemistry, vol. 36(18), pp. 3898-3910, 1997.*

* cited by examiner

*Primary Examiner*—D. Margaret Seaman
(74) *Attorney, Agent, or Firm*—Browdy and Neimark, P.L.L.C.

(57) ABSTRACT

Highly sensitive fluorescent zinc or cadmium sensors are derived from 8-hydroxyquinaldine, a well-established fluorescent zinc probe, as a building block. High binding efficiency was achieved by incorporating two 8-hydroxyquninaldine moieties into a single ligand. Incorporation of sulfonamide groups further improved binding efficiency. The compounds make it possible to monitor zinc ion or cadmium ion concentration in the picomolar or femtomolar range.

3 Claims, 20 Drawing Sheets

8-HYDROXYQUINOLINE TRIPODAL METAL ION PROBES

FIELD OF THE INVENTION

The present invention is directed to fluorescent ligands capable of strongly binding Zn(II) ions or Cd(II) ions.

BACKGROUND OF THE INVENTION

The selective and quantitative detection of trace amounts of Zn(II) or Cd(II) is commercially desirable for the diagnosis of metal ion induced diseases and in protecting the environment.

Zinc is an essential element which is present in the body at approximately 1 micromole/L. The USDA recommended dietary intake of Zn(II) is only 15 mg/day, which indicates how little Zn(II) is required to maintain the required level of this element in a healthy adult. Despite this relatively low concentration, Zn(II) plays an essential role in biology and nutrition. Minor perturbations of normal Zn(II) levels have been associated with retarded sexual maturation, stunted growth, and skin damage. Over 99% of Zn(II) in biological tissues and fluids is present in a chemically combined form, with very little present as free Zn(II). Traditional methods such as atomic absorption effectively measure total Zn(II) but cannot distinguish between the chemically combined and the free forms. The problem of detecting free Zn(II) is compounded because total free Zn(II) is decreased only very slightly (50-100 pmol/$10^6$ cells) in cases of severe Zn(II) deficiency.

Zinc is the second most abundant transition metal in the brain. Zinc is essential for brain maturation and function. Approximately ninety percent of cellular zinc is bound to metalloproteins, while the remainder is localized at presynaptic vesicles in the ionic or loosely bound form. Vesicular zinc is thought to play an important role in synaptic neurotransmission. Several devastating cerebral disorders, such as Alzheimer's disease, Parkinson's disease, and amyotrophic lateral sclerosis (ALS) are associated with abnormally high vesicular Zn(II) concentration (Cuajungo et al., 1997). Because of its association with major neurological disorders, zinc imaging becomes an increasingly important tool in brain research. In particular, fluorescence microscopy is a very useful technique for monitoring real-time zinc distribution.

Cadmium, both as the free metal and in its compounds, is highly toxic, and has been designated one of the 100 most hazardous substances under Section 110 of the Superfund Amendments and Reauthorization Act of 1986. Poisoning occurs with by ingestion or by inhalation.

Chemical pneumonitis or pulmonary edema may result from acute exposure to cadmium fumes, as oxide or chloride aerosols, at a dose of 5 mg/m3 over an eight hour period. Acute ingestion of cadmium concentrations above about 15 ppm produce symptoms of nausea, vomiting, abdominal cramps, and headache. Possible sources of such poisoning have been traced to cadmium-plated cooking utensils, cadmium solders in water coolers, or from acid juices stored in ceramic pots glazed using cadmium-treated compounds.

Most biological molecules do not fluoresce on their own, so they must be linked with fluorescent molecules, or fluorochromes, in order to create specific fluorescent probes. The feasibility of using fluorescence technology for a particular application is often limited by the availability of an appropriate fluorescent sensor. There are a number of features that are desirable in fluorescent sensors, some of which may or may not be present in any particular sensor.

First, fluorescent sensors should produce a perceptible change in fluorescence upon binding a desired analyte. Second, fluorescent sensors should selectively bind a particular analyte. Third, to allow concentration change to be monitored, fluorescent sensors should have a Kd near the median concentration of the species under investigation. Fourth, fluorescent sensors, especially when used intracellularly, should produce a signal with a high quantum yield. Fifth, the wavelengths of both the light used to excite the fluorescent molecule (excitation wavelengths) and of the emitted light (emission wavelengths) are often important. If possible, for intracellular use, a fluorescent sensor should have excitation wavelengths exceeding 340 nm to permit use with glass microscope objectives and prevent UV-induced cell damage, and possess emission wavelengths approaching 500 nm to avoid autofluorescence from native substances in the cells and allow use with conventional fluorescence microscopy optical filter sets. Finally, ideal sensors should allow for passive and irreversible loading into cells.

Since the Zn(II) ion is spectroscopically silent, fluorescence microscopy for Zn(II) requires a sensor that makes it possible to observe this ion. There are several requirements that a fluorescent sensor for zinc needs to meet. First of all, it must produce a strong fluorescent signal upon binding the analyte. Secondly, the sensor needs to exhibit strong zinc binding, ideally having an apparent dissociation constant, Kd, near the median of Zn(II) concentration. The latter requirement is particularly challenging, given that Zn(II) concentration is known to be as low as femtomolar (Hitomi et al., 2001). Strong selectivity is another important factor in Zn(II) detection, because Zn(II) concentration is typically six to seven orders of magnitude lower than the concentration of the more abundant divalent metal ions such as Mg(II) and Ca(II) (Fraustro da Silva et al., 1993). Finally, there are several biological requirements to prevent cell damage from excitation and emission wavelengths, as noted above. In addition to that, the sensor must be soluble in physiological media.

The detection of Zn(II) or Cd(II) in the environment is also important, and is presently an intractable problem. For example, interest in Zn(II) concentrations in the ocean stems from its dual role as a required nanonutrient and as a potential toxic agent due to its widespread industrial and marine usage. Zinc exists at natural levels in ocean surface water at a total concentration of about 0.1 nM. Dissolved Zn(II) concentrations in seawater have been determined using atomic absorption spectrometry, mass spectrometry and voltammetry. The concentration data are inaccurate because of interference from other cations naturally present in sea water. A rapid, selective an more sensitive test for Zn(II) or Cd(II) is desirable.

A limited number of fluorescent sensors possess these desirable properties.

SUMMARY OF THE INVENTION

It is an object of the present invention to overcome the aforesaid deficiencies in the prior art.

It is another object of the present invention to provide fluorescent ligands capable of strongly binding Zn(II) or Cd(II).

It is still another object of the present invention to provide enhanced zinc or cadmium binding along with fluorescence sensing capabilities.

It is yet another object of the present invention to provide improved methods of detecting Zn(II) or Cd(II) in the presence of other divalent metals.

The present invention provides fluorescent ligands which are capable of strongly binding Zn(II) or Cd(II) in the presence of other divalent metal ions. These tripodal ligands, illustrated by the compounds shown in FIGS. 1 to 3, are structurally related to tris(2-pyridylmethyl)amine, TPA, which is known for strong binding of divalent metal ions (Anderegg et al., 1967).

A and B can be the same or different, and are

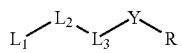

Wherein $L_1$, $L_2$, and $L_3$ can be the same or different, and $L_1$, $L_2$ and $L_3$ are linker groups selected from the group consisting of substituted or unsubstituted carbon atoms, —O—, —S—, —$NR_2$, $C_6$-$C_{24}$ substituted or unsubstituted aromatic and heteroaromatic groups having from 1-3 heteroatoms (N, S, O) or halogen, carbonyl, sulfonyl, or nitrile substitutions, and $L_2$ and $L_3$ are optional groups. $L_1$ and Y can be part of a ring such as pyridine or other heteroaromatic ring.

R is a terminal group selected form the group consisting of H, $C_1$-$C_{18}$ branched or straight-chain alkyl, alkenyl, or alkynyl groups groups, $C_6$-$C_{24}$ substituted or unsubstituted aromatic and heteroaromatic groups having from 1-3 hetero atoms (N, S, O) or halogen substitutions.

X is HO or NHR

Y is a metal chelating atom such as N, O, or S

E is a hydrogen atom or a substituent of the aromatic ring, such as halogen, carbonyl, sulfonyl, or nitrile.

As used herein, alkyl, alkenyl and alkynyl carbon chains, if not specified, contain from 1 to 20 carbon atoms, preferably from 1 to 16 carbon atoms, and are straight or branched. Alkenyl carbon chains of from 1 to 20 carbon atoms preferably contain 1 to 8 double bonds; the alkenyl carbon chains of 1 to 16 carbon atoms preferably contain from 1 to 5 double bonds.

Alkynyl carbon chains of from 1 to 20 carbon atoms preferably contain 1 to 8 triple bonds, and the alkynyl carbon chains of 1 to 16 carbon atoms preferably contain 1 to 5 triple bonds. The alkyl, alkenyl, and alkynyl groups may be optionally substituted, with one or more groups, preferably alkyl group substituents that may be the same or different. As used herein, lower alkyl, lower alkenyl, and lower alkynyl refer to carbon chains having fewer than or equal to about 6 carbon atoms.

As used herein an alkyl group substituent includes halos, haloalkyl, preferably halo lower alkyl, aryl, hydroxy, alkoxy, aryloxy, alkoxy, alkylthio, arylthio, aralkyloxy, aralkylthio, carboxy, alkoxycarbonyl, oxo, and cycloalkyl.

For the present invention, "cyclic" refers to cyclic groups preferably containing from 3 to 19 carbon atoms, preferably 3 to 10 members, more preferably 5 to 7 members. Cyclic groups include hetero atoms, and may include bridged rings, fused rings, either heterocyclic, cyclic, or aryl rings.

The term "aryl" herein refers to aromatic cyclic compounds having up to 10 atoms, including carbon atoms, oxygen atoms, sulfur atoms, selenium atoms, etc. Aryl groups include, but are not limited to, groups such as phenyl, substituted phenyl, naphthyl, substituted naphthyl, in which the substituent is preferably lower alkyl, halogen, or lower alkyl. "Aryl" may also refer to fused rings systems having aromatic unsaturation. The fused ring systems can contain up to about 7 rings.

An "aryl group substituent" as used herein includes alkyl, cycloalkyl, cycloaryl, aryl, heteroaryl, optionally substituted with 1 or more, preferably 1 to 3, substituents selected from halo, haloalkyl, and alkyl, arylalkyl, heteroarylalkyl, alkenyl containing 1 to 2 double bonds, alkynyl containing 1 to 2 triple bonds, halo, hydroxy, polyhaloalkyl, preferably trifluoromethyl, formyl, alkylcarbonyl, arylcarbonyl, optionally substituted with 1 or more, preferably 1 to 3, substituents selected from halo, haloalkyl, alkyl, heteroarylcarbonyl, carboxyl, alkoxycarbonyl, aryloxycarbonyl, aminocarbonyl, alkylaminocarbonyl, dialkylaminocarbonyl, arylalkylaminocarbonyl, alkoxy, aryloxy, perfluoroalkoxy, alkenyloxy, alkynyloxy, arylalkoxy, aminoalkyl, alkylaminoalkyl, dialkylaminoalkyl, arylaminoalkyl, amino, alkylamino, dialkylamino, arylamino, alkylarylamino, alkylcarbonylamino, arylcarbonylamino, amido, nitro, mercapto, alkylthio, arylthio, perfluoroalkylthio, thiocyano, isothiocyano, alkylsufinyl, alkylsulfonyl, arylsulfinyl, arylsulfonyl, aminosulfonyl, alkylaminosulfinyl, dialkylaminosulfonyl, and arylaminosulfonyl.

The term "arylalkyl" as used herein refers to an alkyl group which is substituted with one or more aryl groups. Examples of arylalkyl groups include benzyl, 9-fluorenylmethyl, naphthylmethyl, diphenylmethyl, and triphenylmethyl.

The term "heteroaryl" for purposes of the present application refers to a monocyclic or multicyclic ring system, preferably about 5 to about 15 members, in which at least one atom, preferably 1 to 3 atoms, is a heteroatom, that is, an element other than carbon, including nitrogen, oxygen, or sulfur atoms. The heteroaryl may be optionally substituted with one or more, preferably 1 to 3, aryl group substituents. Exemplary heteroaryl groups include, for example, furanyl, thienyl, pyridyl, pyrrolyl, N-methylpyrrolyl, quinolyinyl and isoquinolinyl.

The term "heterocyclic" refers to a monocyclic or multicyclic ring system, preferably of 3 to 10 members, more preferably 4 to 7 members, where one or more, preferably 1 to 3, of the atoms in the ring system is a heteroatom, i.e., an atom that is other than carbon, such as nitrogen, oxygen, or sulfur. The heterocycle may be optionally substituted with one or more, preferably 1 to 3, aryl group substituents. Preferred substituents of the heterocyclic group include hydroxy, alkoxy, halo lower alkyl. The term heterocyclic may include heteroaryl. Exemplary heterocyclics include, for example, pyrrolidinyl, piperidinyl, alkylpiperidinyl, morpholinyl, oxadiazolyl, or triazolyl.

The nomenclature alkyl, alkoxy, carbonyl, etc, is used as is generally understood by those of skilled this art. As used herein, aryl refers to saturated carbon chains that contain one or more carbon atoms; the chains may be straight or branched or include cyclic portions or may be cyclic.

The term "halogen" or "halide" includes F, Cl, Br, and I. This can include pseudohalides, which are anions that behave substantially similarly to halides. These compounds can be used in the same manner and treated in the same manner as halides. Pseudohalides include, but are not limited to, cyanide, cyanate, thiocyanate, selenocyanate, trifluoromethyl, and azide.

The term "sulfinyl" refers to —S(O)—. "sulfonyl" refers to —$S(O)_2$—.

"Aminocarbonyl" refers to —$C(O)NH_2$.

"Alkylene" refers to a straight, branched, or cyclic, preferably straight or branched, bivalent aliphatic hydrocarbon group, preferably having from 1 to about 20 carbon atoms. The alkylene group is optionally substituted with one or more alkyl group substituents. There may be optionally inserted along the alkylene group one or more oxygen, sulfur, or substituted or unsubstituted nitrogen atoms, wherein the nitrogen substituent is alkyl. Exemplary alkylene groups include methylene, ethylene, propylene, cyclohexylene, methylenedioxy, and ethylenedioxy. The term "lower alkylene" refers to alkylene groups having from 1 to 6 carbon atoms. Preferred alkylene groups are lower alkylene, with alkylene of 1 to 3 atoms being particularly preferred.

The term "arylene" as used herein refers to a monocyclic or polycyclic bivalent aromatic group preferably having from 1 to 20 carbon atoms and at least one aromatic ring. The arylene group is optionally substituted with one or more alkyl group substituents. There may be optionally inserted around the arylene group one or more oxygen, sulfur, or substituted or unsubstituted nitrogen atoms, where the nitrogen substituent is alkyl.

"Heteroarylene" refers to a bivalent monocyclic or multicyclic ring system, preferably of about 5 to about 15 members, wherein one or more of the atoms in the ring system is a heteroatom. The heteroarylene may be optionally substituted with one or more aryl group substituents. As used herein, "alkylidene" refers to a bivalent group, such as =CR'R", which is attached to one atom of another group, forming a double bond. "Arylalkylidene" refers to an alkylidene group in which either R' or R" is an aryl group.

As used herein, when any particular group, such as phenyl or pyridyl, is specified, this means that the group is substituted or unsubstituted. Preferred substituents, where not specified, are halo, halo lower alkyl, and lower alkyl.

The novelty of the design of the compounds of the present invention is in modifying the scaffold structure of TPA with the elements of 8-hydroxyquinoline (8-HQ), as illustrated in FIG. 4. This modification made it possible to further enhance zinc or cadmium binding in addition to providing fluorescence sensing capabilities. In order to improve spectroscopic properties, the 8-HQ chromophore was derivatized with dimethyl sulfonamide groups. This derivatization had been reported to enhance extinction coefficient and fluorescence yield (Pearce et al., 2001).

Enhancement of fluorescence was observed upon zinc or cadmium chelation. Moderate enhancement of 4-fold was observed in the case of TRS. TRS2 and TRSS2, on the other hand, exhibited stronger fluorescent enhancement, 10-fold and 25-fold, respectively.

DETAILED DESCRIPTION OF THE INVENTION

Figure 1:
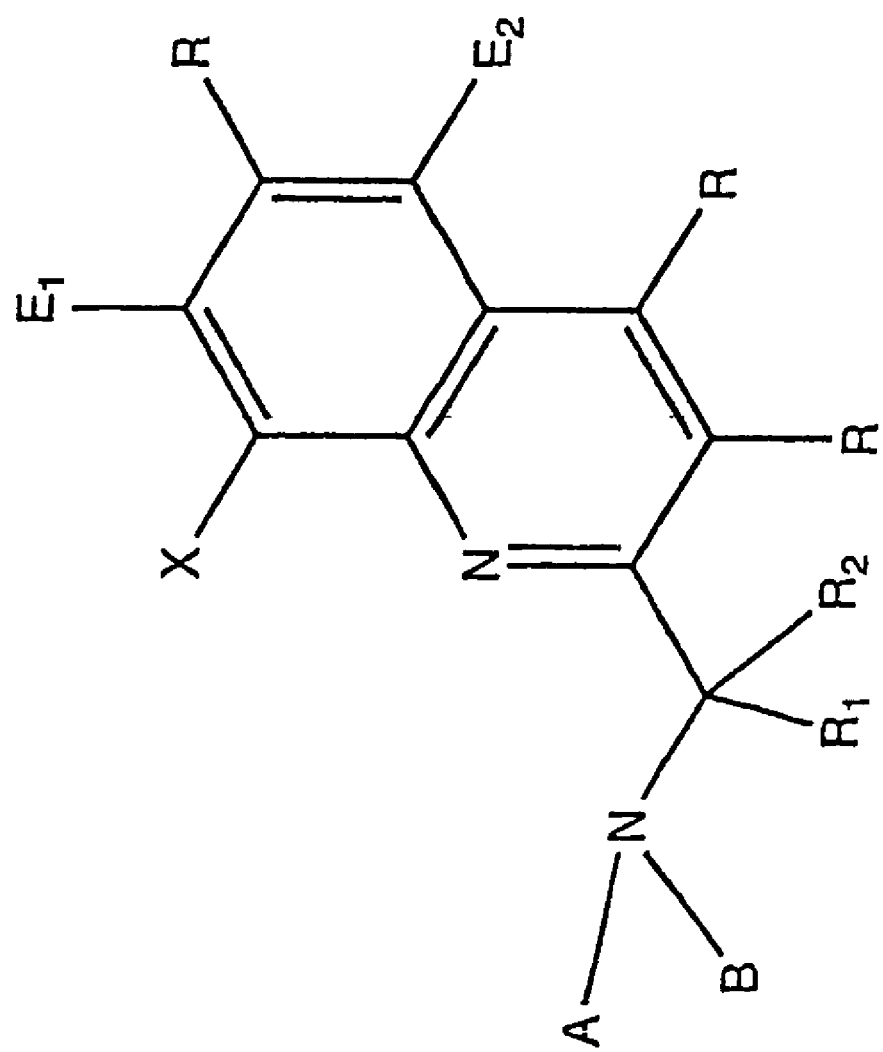
FIG. 1 is the general formula for tripodal ligands of the present invention.
Figure 2:
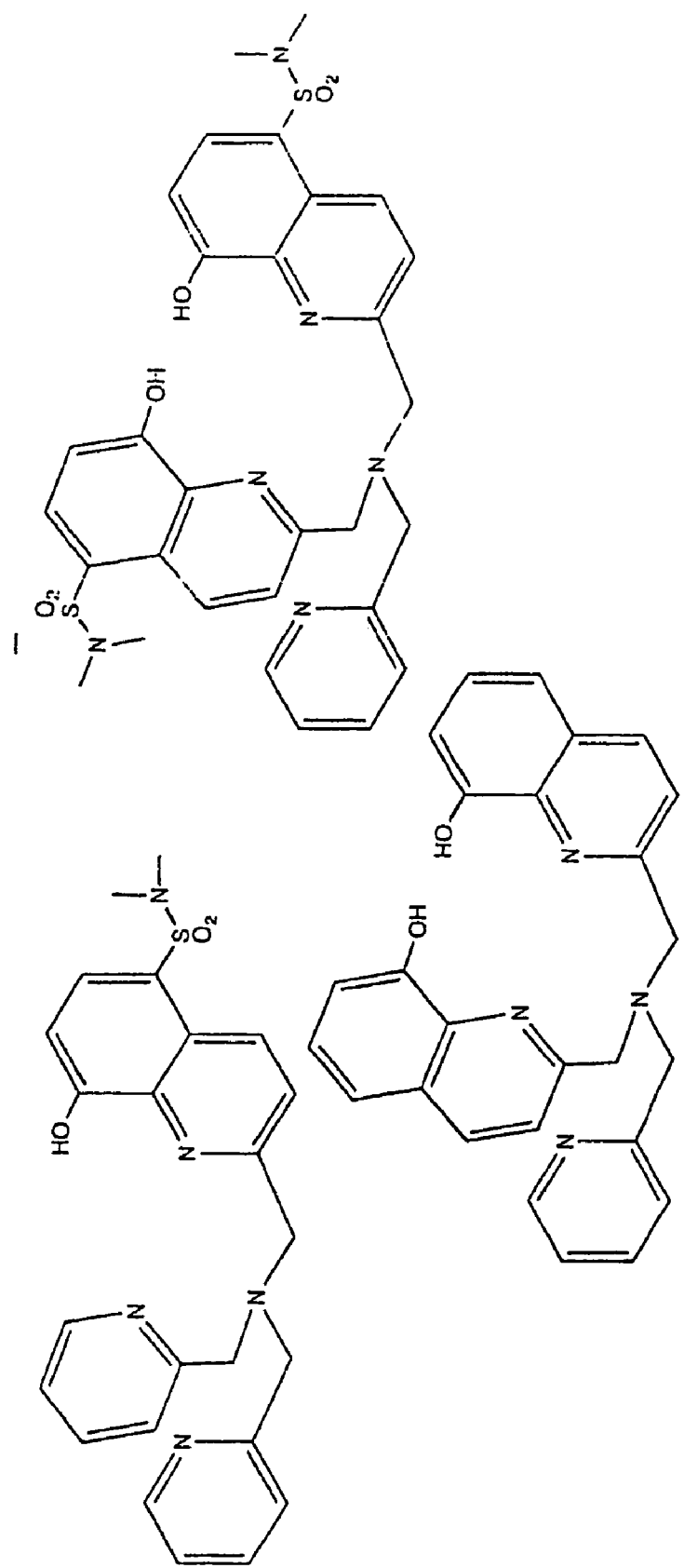
FIG. 2 illustrates three tripodal ligands of the present invention.

The most important property exhibited by the tripodal ligands of the present invention is strong preferential binding of Zn(II). This strength of binding is similar to the one observed in zinc enzymes. The binding constant of TRS was found to be log K1=13.77, which falls within the median physiological zinc concentration. TRS would be able to sense Zn(II) at femtomolar concentrations. TRS2 and TRSS2 showed subpicomolar sensitivity towards Zn(II) with binding constants log K1=12.53 and log K1=13.29, respectively.

Selectivity for zinc over biologically abundant metals such as calcium, magnesium, sodium and potassium was observed.

The fluorescent zinc or cadmium sensors of the present invention are highly sensitive towards the analyte. Their sensitivity (femtomolar to sub-picomolar) lies within the concentration range of physiologically occurring Zn(II) or Cd(II). Therefore, these sensors can be used as quantitative zinc probes in fluorescence microscopy. These tripodal ligands can offer a clear advantage for imaging cellular zinc or cadmium, as well as trace amounts of these metals in environmental samples.

The fluorescence of ligands of the present invention may be detected by essentially any suitable fluorescence detection device. Such devices are typically comprised of a light source for excitation of the fluorophore and a sensor for detecting emitted light. In addition, fluorescence detection devices typically contain a means for controlling the wavelength of the excitation light and a means for controlling the wavelength of light detected by the sensor. These means for controlling wavelengths are referred to generally as filters, and can include diffraction gratings, dichroic mirrors, or filters. Examples of suitable devices include fluorimeters, spectrofluorimeters, and fluorescence microscopes. Many such devices are commercially available. In certain embodiments, the device may be coupled to a signal amplifier and a computer for data processing.

In general, assays using the tripodal ligands of the present invention involve contacting a sample with such a ligand and measuring fluorescence emitted. The presence of Zn(II) or Cd(II) may alter the fluorescence in many different ways. Essentially any change in fluorescence caused by the Zn(II) or Cd(II) can be used to determine the presence of the Zn(II) or Cd(II) and, optionally the concentration of the Zn(II) or Cd(II) in the sample.

The change in fluorescence may take one or more of several forms, including a change in excitation or emission spectra, or a change in the intensity of the fluorescence and/or quantum yield. These changes may be in the positive or negative direction, and may be of a range of magnitudes.

The excitation spectrum is the wavelengths of light capable of causing the ligand to fluoresce. To determine the excitation spectrum for a ligand in a sample, different wavelengths of light are tested sequentially for their abilities to excite the sample. For each excitation wavelength tested, emitted light is measured. Emitted light may be measured across an interval of wavelengths (for example from 450 to 700 nm), or emitted light may be measured as total of all light with wavelengths above a certain threshold (for example, wavelengths greater than 500 nm). A profile is produced of the emitted light produced in response to each tested excitation wavelength, and the point of maximum emitted light can be referred to as the maximum excitation wavelength. A change in this maximum excitation wavelength, or a change in the shape of the profile caused by metal in a sample may be used as the basis for determining the presence, and optionally, the concentration, of Zn(II) or Cd(II) in the sample. Alternatively, the emission spectrum may be determined by examining the spectra of emitted light in response to excitation with a particular wavelength (or interval of wavelengths). A profile of emissions at different wavelengths is created, and the wavelength at which emission is maximal is called the maximum emission wavelength. Changes in the maximum emission wavelength or the shape of the profile that are caused by the presence of Zn(II) or Cd(II) in a sample may be used to determine the presence or concentration of the metal ion in the sample. Changes in excitation or emission spectra may be measured as ratios of two wavelengths. A range of changes is possible, from about a few nms to 5, 20, 25, 50, 75, 100 or more nm.

In Vitro Assays

In one embodiment of the present invention, the presence of Zn(II) or Cd(II) in a sample is detected by contacting the sample with a tripodal ligand according to the present invention. The fluorescence of the solution is then determined using one of the above-described devices, preferably a spectofluorimeter. Optionally, the fluorescence of the solution may be compared to a set of standard solutions containing known quantities of Zn(II) or Cd(II). Comparison to standards may be used to calculate the concentration of Zn(II) or Cd(II).

Although the tripodal ligands are particularly useful for detecting small quantities of Zn(II) or Cd(II) in physiological specimens such as brain tissue for diagnosing neurological diseases such as Alzheimer's and Parkinson's diseases, they can also be used to detect small quantities of Zn(II) or Cd(II) in environmental samples such as water samples, soil leachates, or sediment samples.

In Vivo Assays

Biological samples may include bacterial or eukaryotic cells, tissue samples, lysates, or fluids from a living organism. In certain embodiments, the specimens are brain tissues. It is also anticipated that detection of Zn(II) or Cd(II) in a cell may include detection of the metal in subcellular or extracellular compartments or organelles. Such subcellular organelles and compartments include: Golgi networks and vesicles, pre-synaptic vesicles, lysosomes, vacuoles, nuclei, chromatin, mitochondria, chloroplasts, endoplasmic reticulum, coated vesicles (including clathrin coated vesicles), caveolae, peroplasmic space, and extracellular matrices.

Assays Using the Subject Compounds

The solution or biological sample is contacted with a tripodal ligand according to the present invention, and fluorescence of the ligand is excited by light with wavelengths ranging from 340 nm to about 380 nm. Light emitted by the ligand is detected by detecting light of wavelengths greater than from about 480 to about 600 nm.

Synthesis of the Tripodal Ligands

Figure 3:
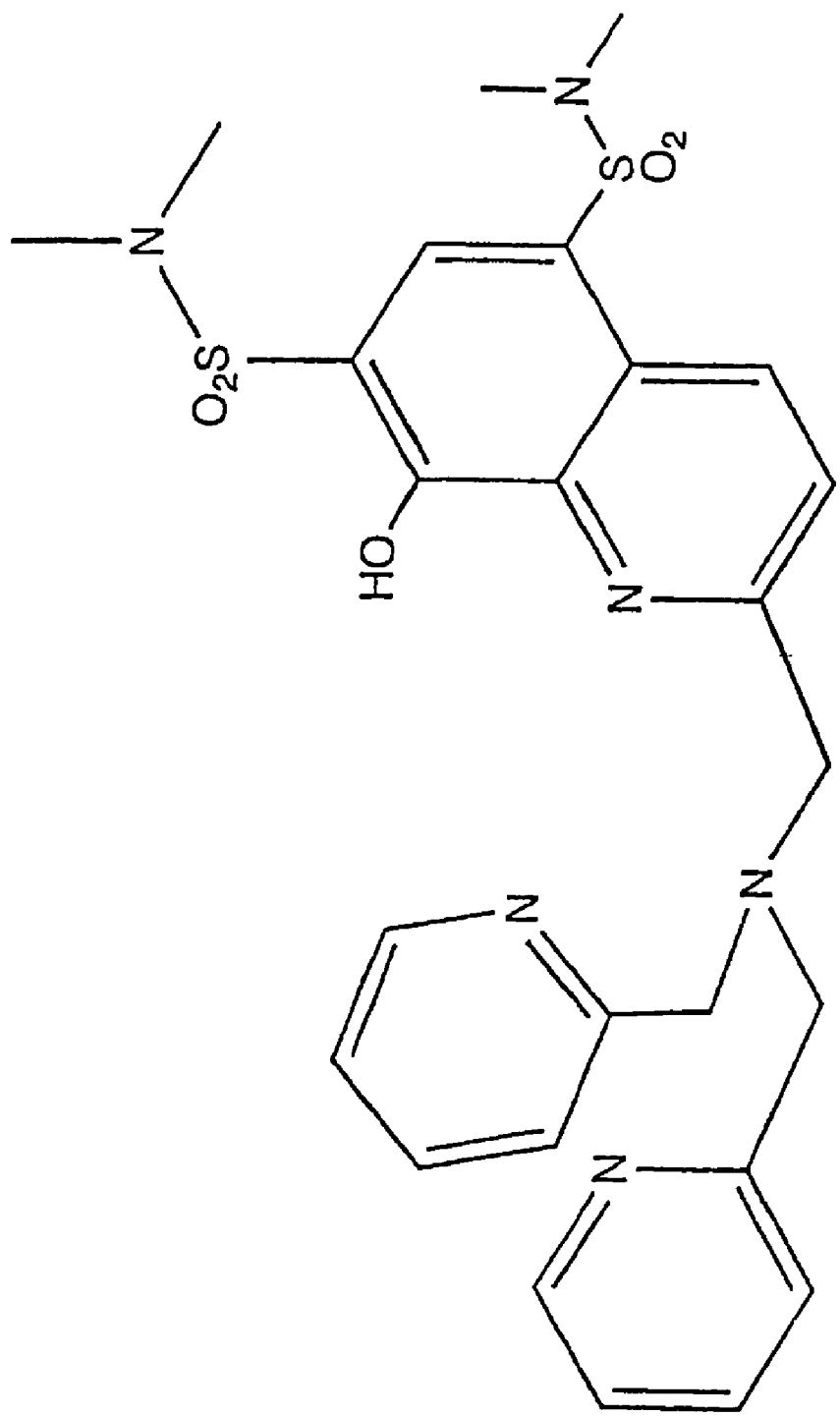
FIG. 3 illustrates another tripodal zinc sensor of the present invention.
Figure 4:
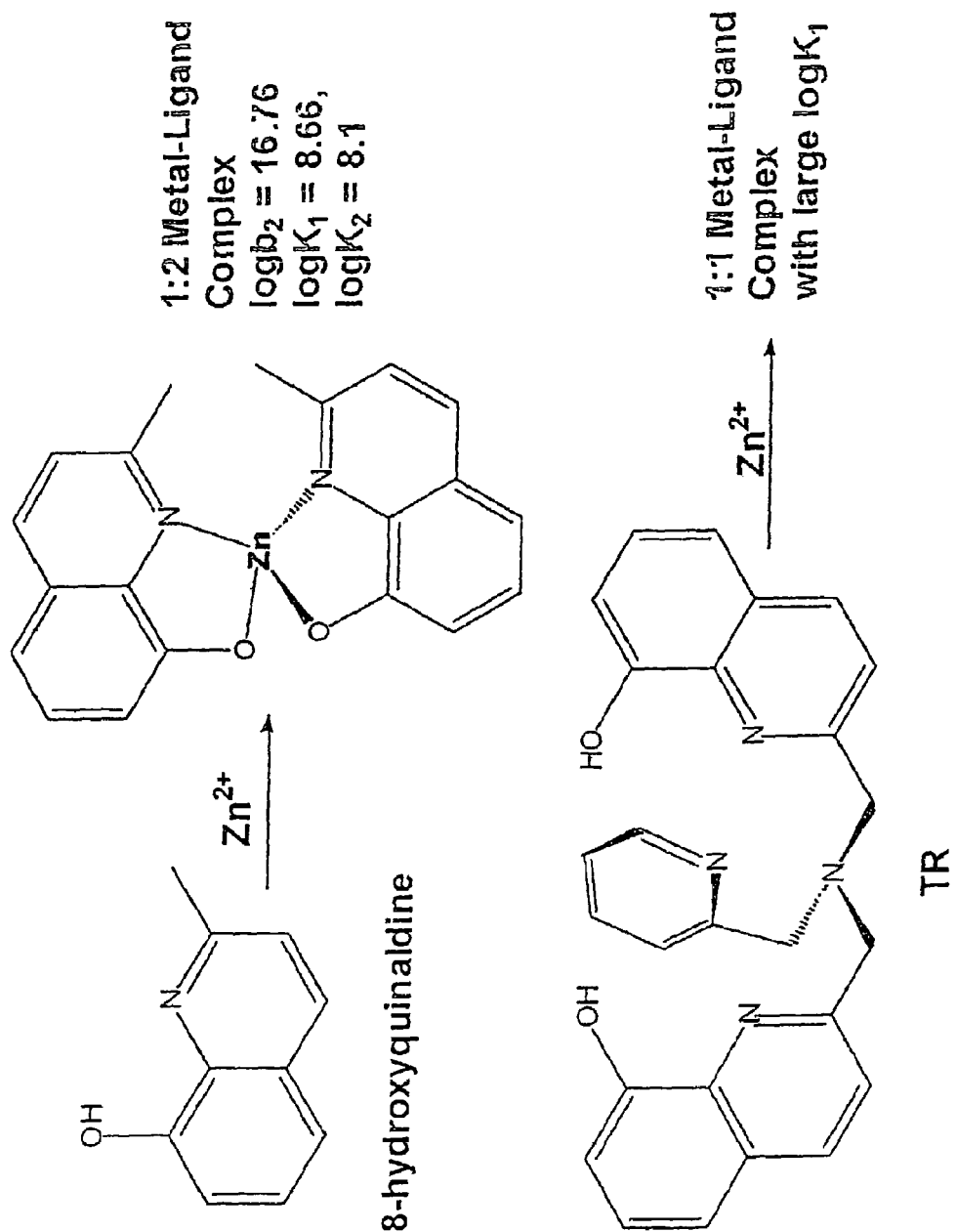
FIG. 4 illustrates design of the sensors from 8-hydroxyquinaldine.
Figure 5:
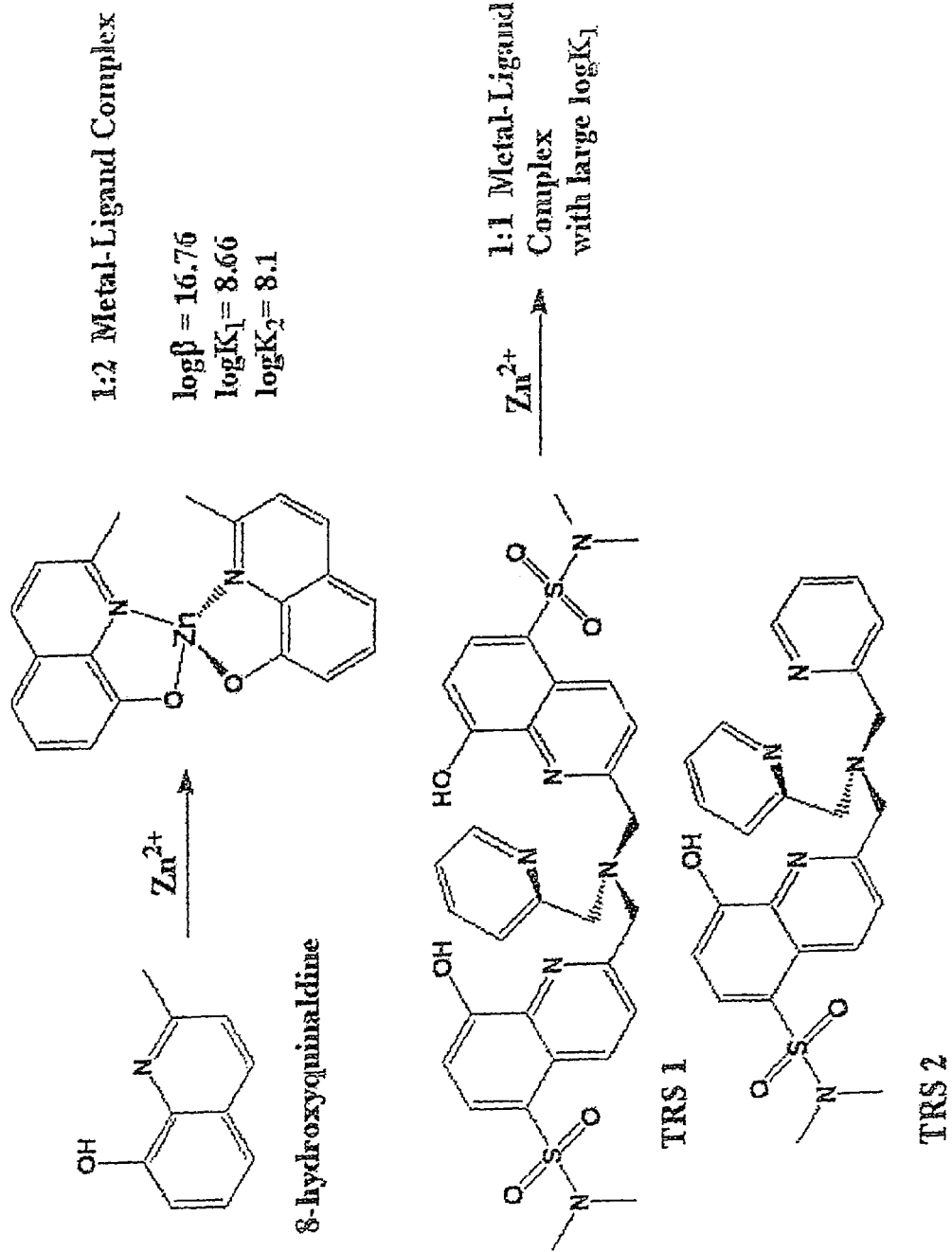
FIG. 5 illustrates design of the sensors from 8-hydroxyquinaldine.
Figure 6:
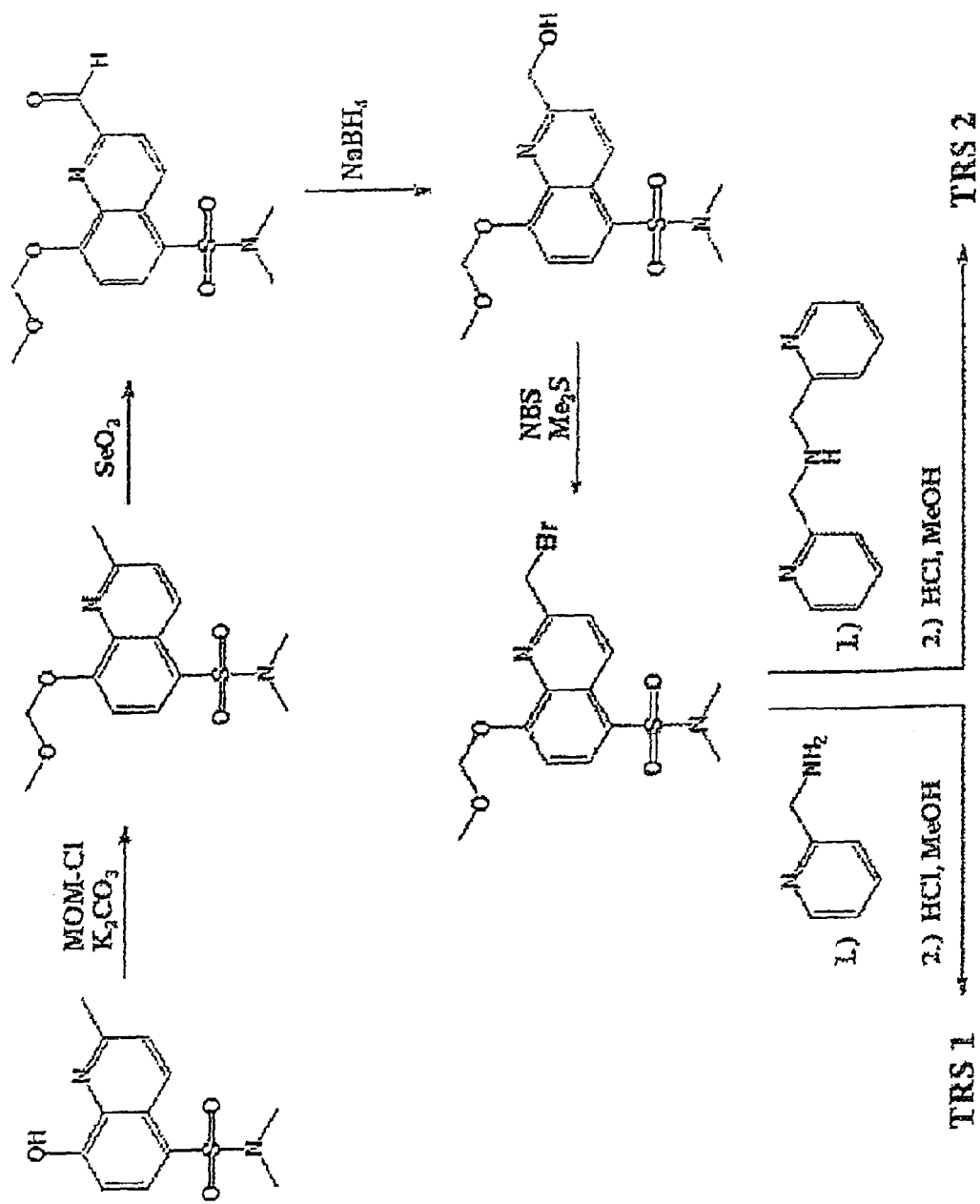
FIG. 6 illustrates synthesis of two of the compounds of the present invention.
Figure 14:
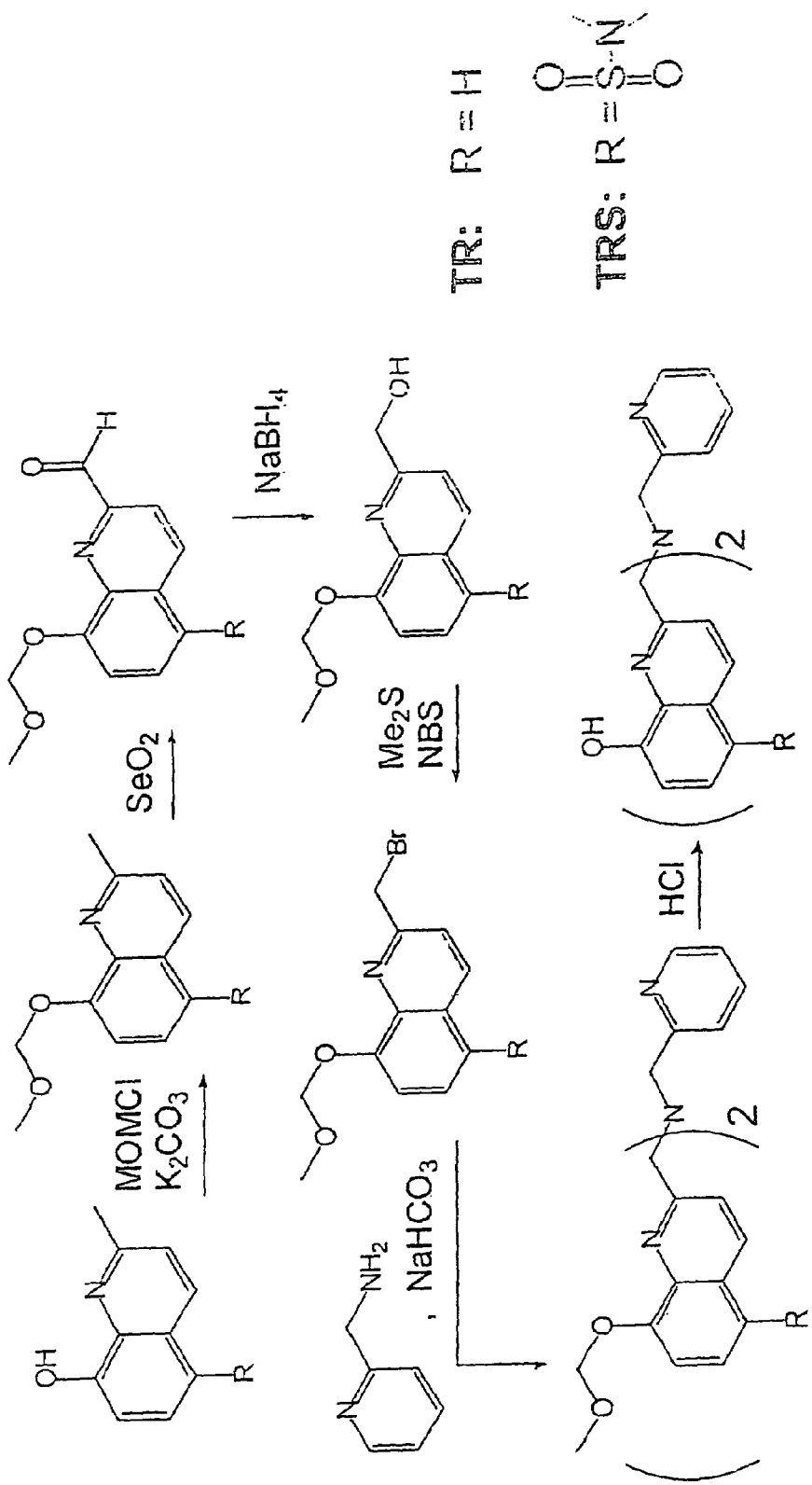
FIG. 14 illustrates synthesis of two of the compounds of the present invention.
Figure 15:
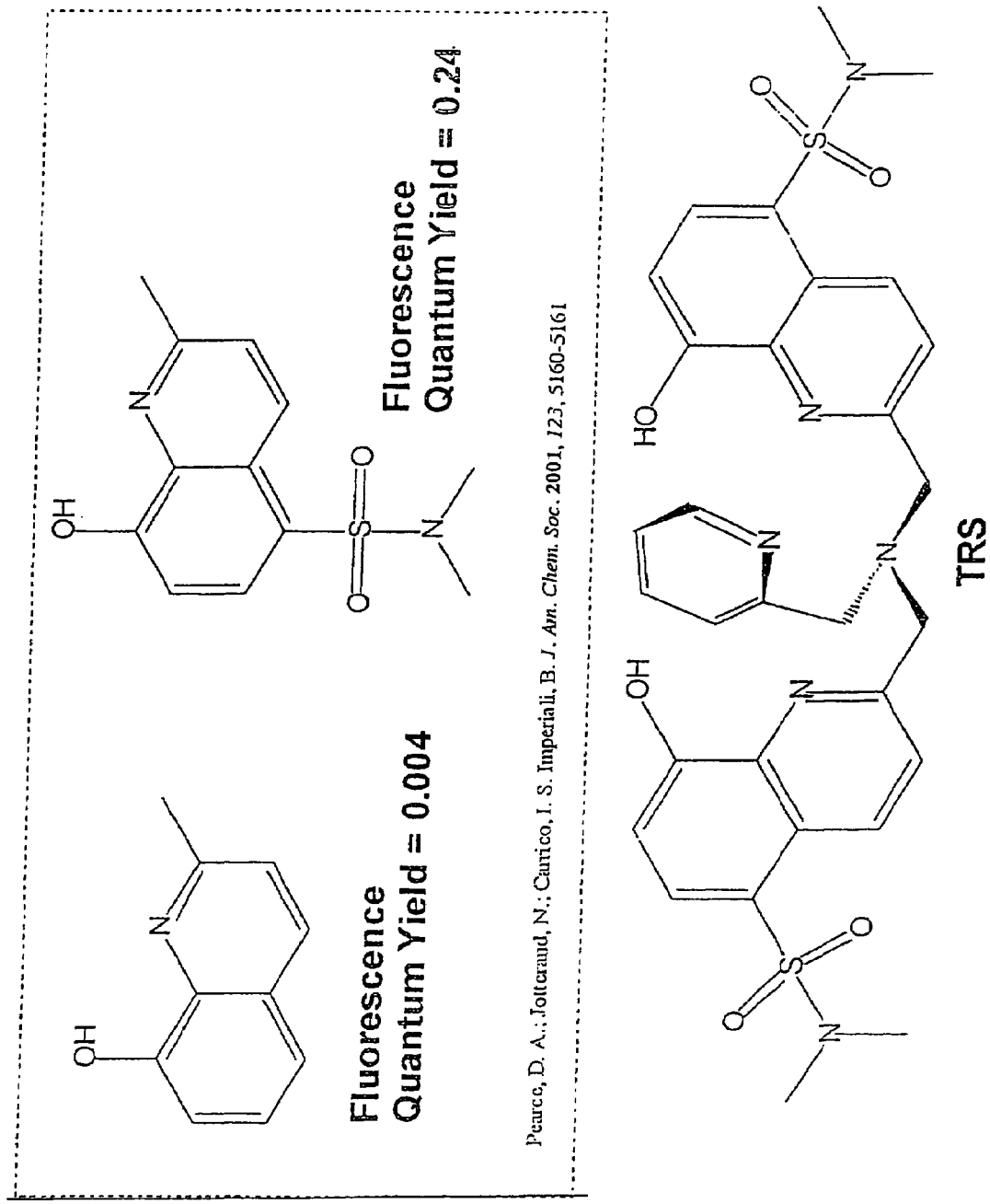
FIG. 15 illustrates how the compounds of the present invention improve the fluorescence quantum yield of the 8-hydroxyquinoline derivatives.

FIGS. 6 and 14 illustrate the structural design of the tripodal ligands of the present invention. The scaffold structure of TPA is modified with the elements of 8-hydroxyquinoline. It was discovered that the most active compound was the compound TRS, shown in FIG. 3, the compound with two sulfonamide groups attached to the 8-hydroxyquinoline.

Figure 7:
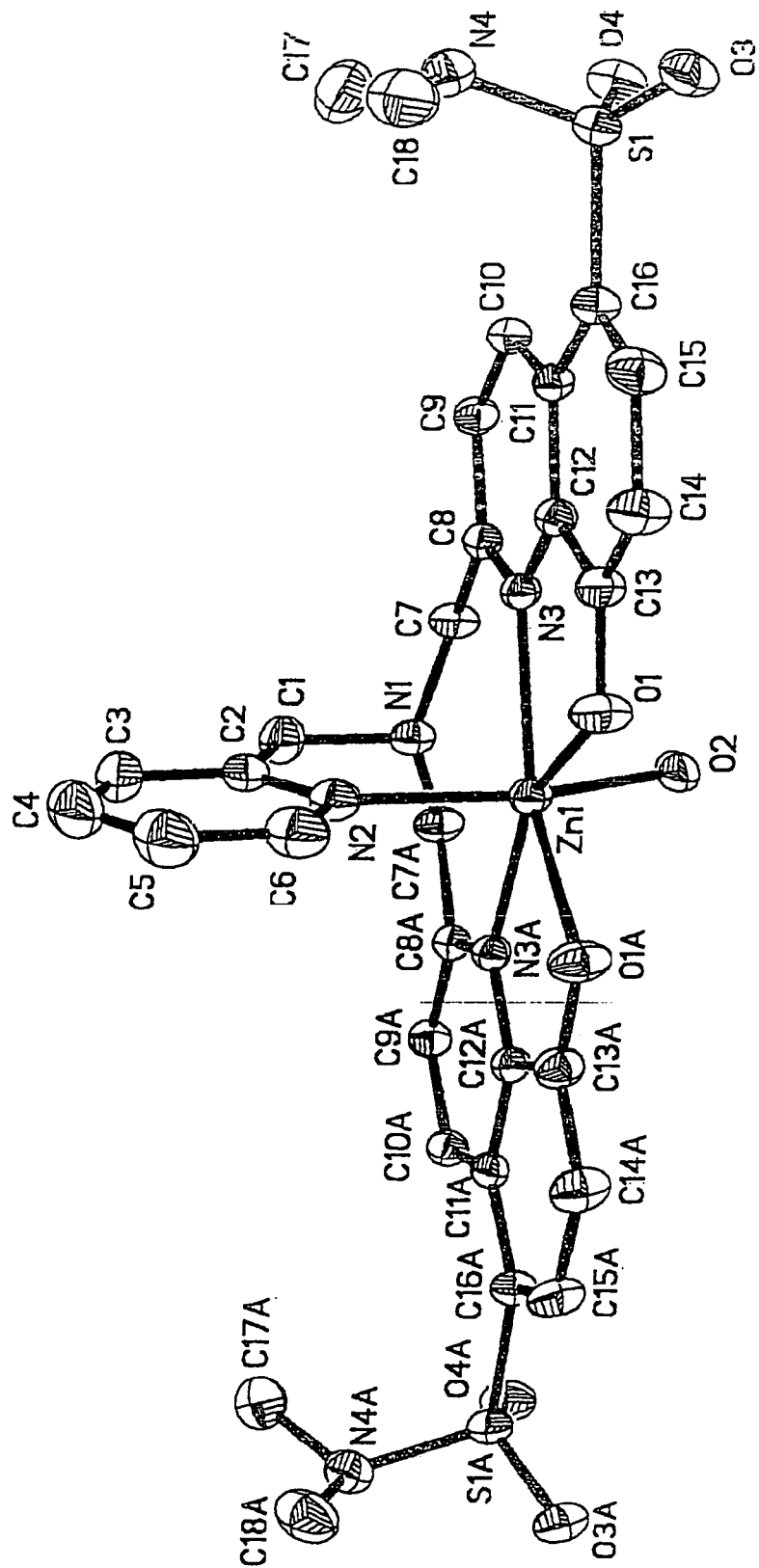
FIG. 7 shows the X-ray structure of Zn(TRS 1).

As shown in FIG. 7, zinc makes four coordinations with the two 8-hydroxyquinoline moieties, and one coordination with the pyridyl nitrogen.

Figure 8:
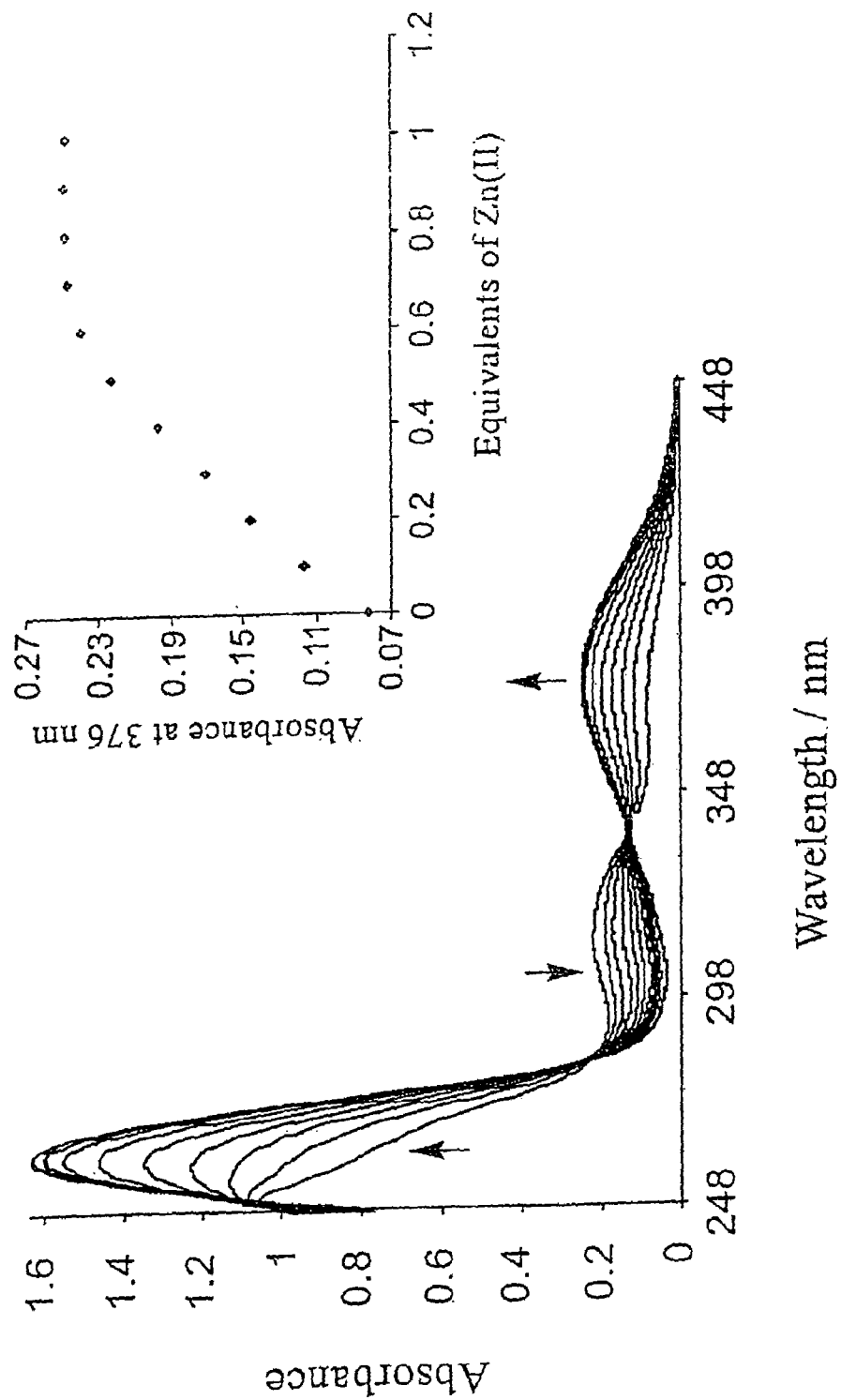
FIG. 8 shows the UV-visible absorbance of TRS 2 as function of zinc (II) concentration.
Figure 9:
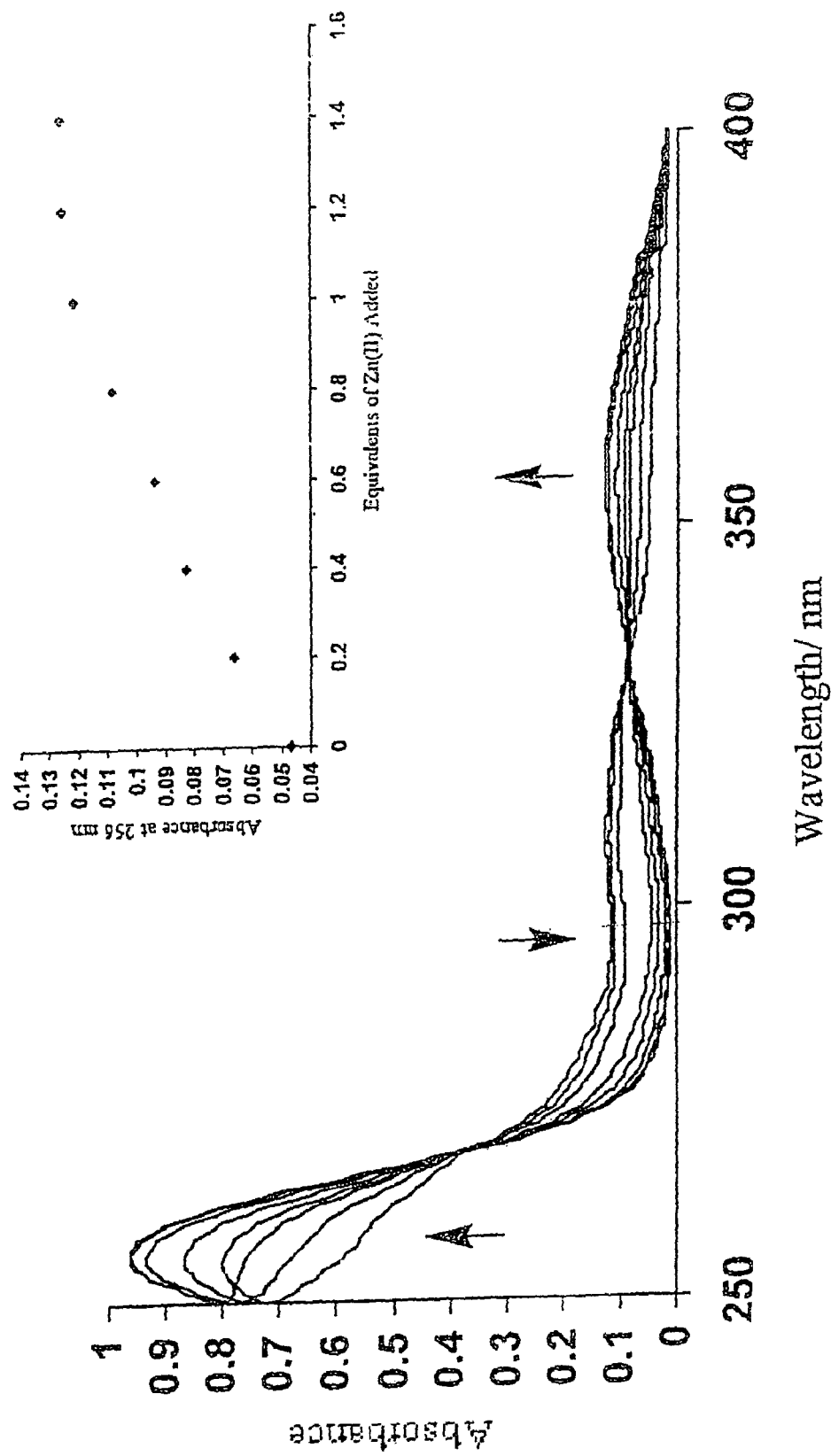
FIG. 9 shows the UV-visible absorbance of TRS 1 as function of zinc (II) concentration.

FIGS. 8 and 9 show the UV-visible absorbance of TRS 1 and TRS 2, respectively, 30 micromolar, as a function of Zn(II) concentration. The spectra were acquired in 1% DMSO aqueous solution (0.1 M KNO3, 50 mM HEPES, pH 7.0). The inset in both of these figures is a molar ratio plot of Zn(II).

Figure 10:
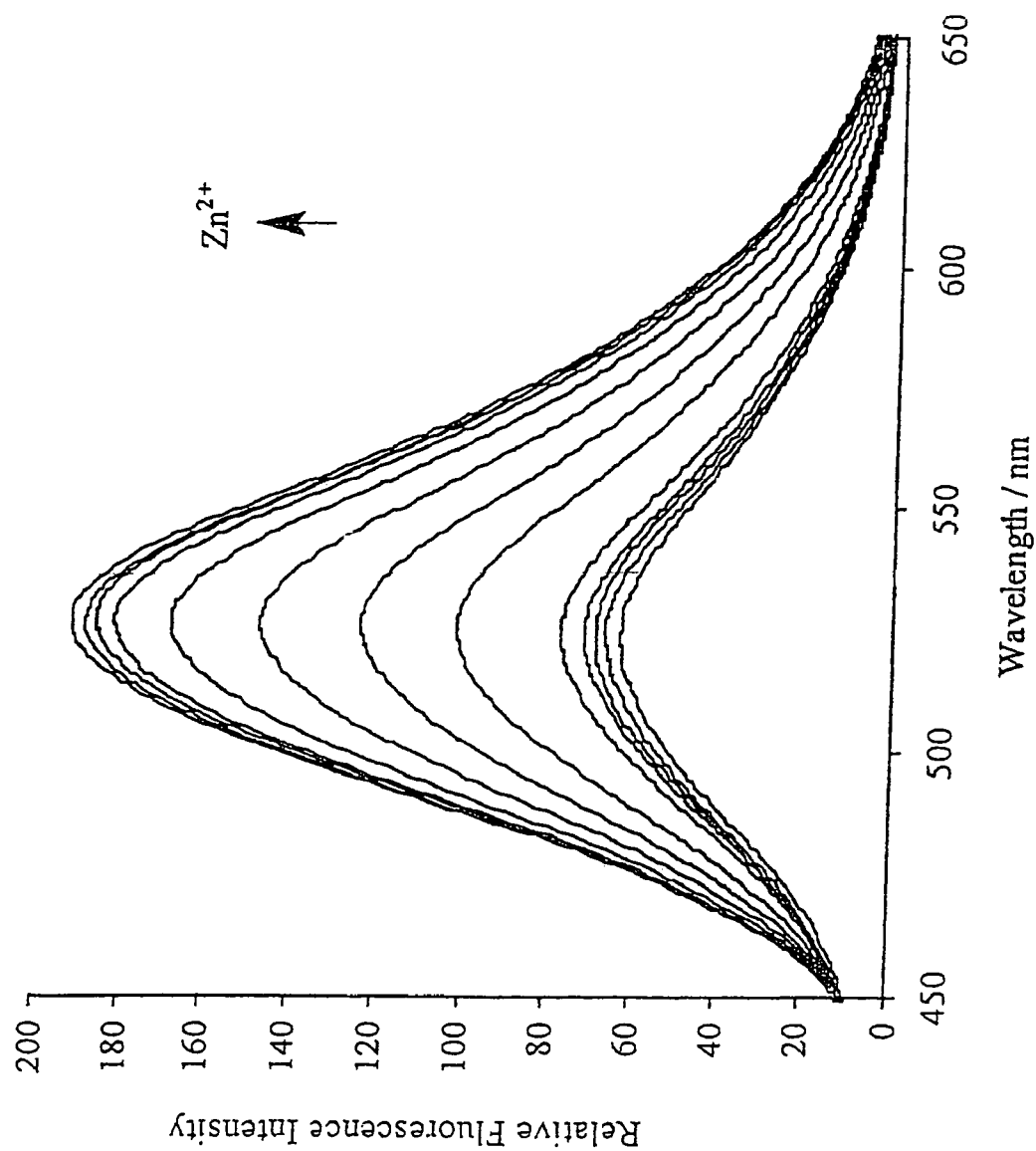
FIG. 10 shows the fluorescence response of TRS 2 to buffered Zn(II) solutions.
Figure 11:
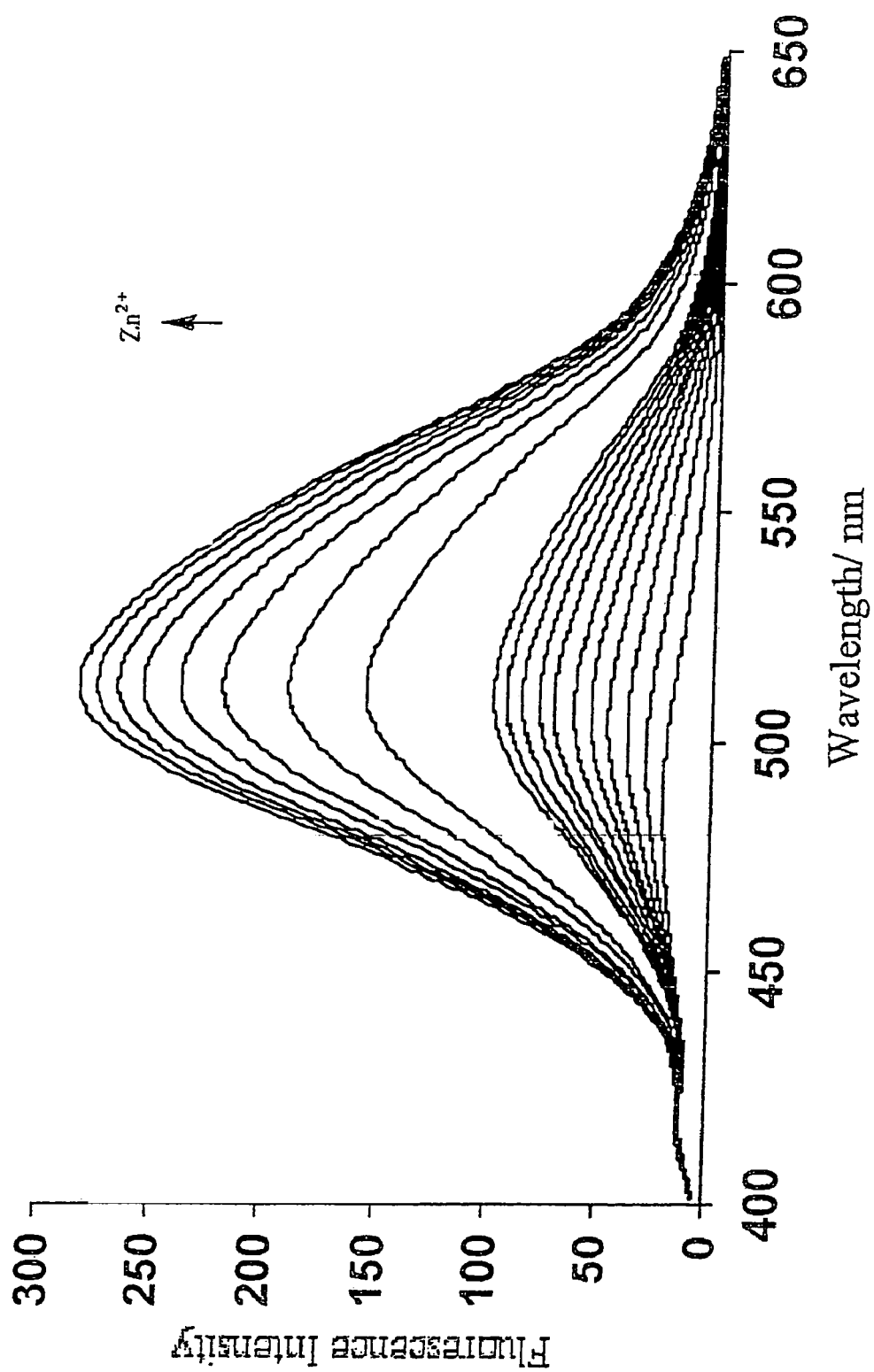
FIG. 11 shows the fluorescence response of TRS 2 to buffered Zn(II) solutions.

FIGS. 10 and 11 show the fluorescence response of 30 micromolar TRS 1 and TRS 2, respectively, to buffered Zn(II) solutions. The spectra were acquired in 1% DMSO aqueous solution (0.1 M $KNO_3$, 50 mM HEPES, pH 7.2 at 25° C.) with excitation at 365 nm. The zinc ion concentration was buffered by 10 mM EDTA.

Figure 12:
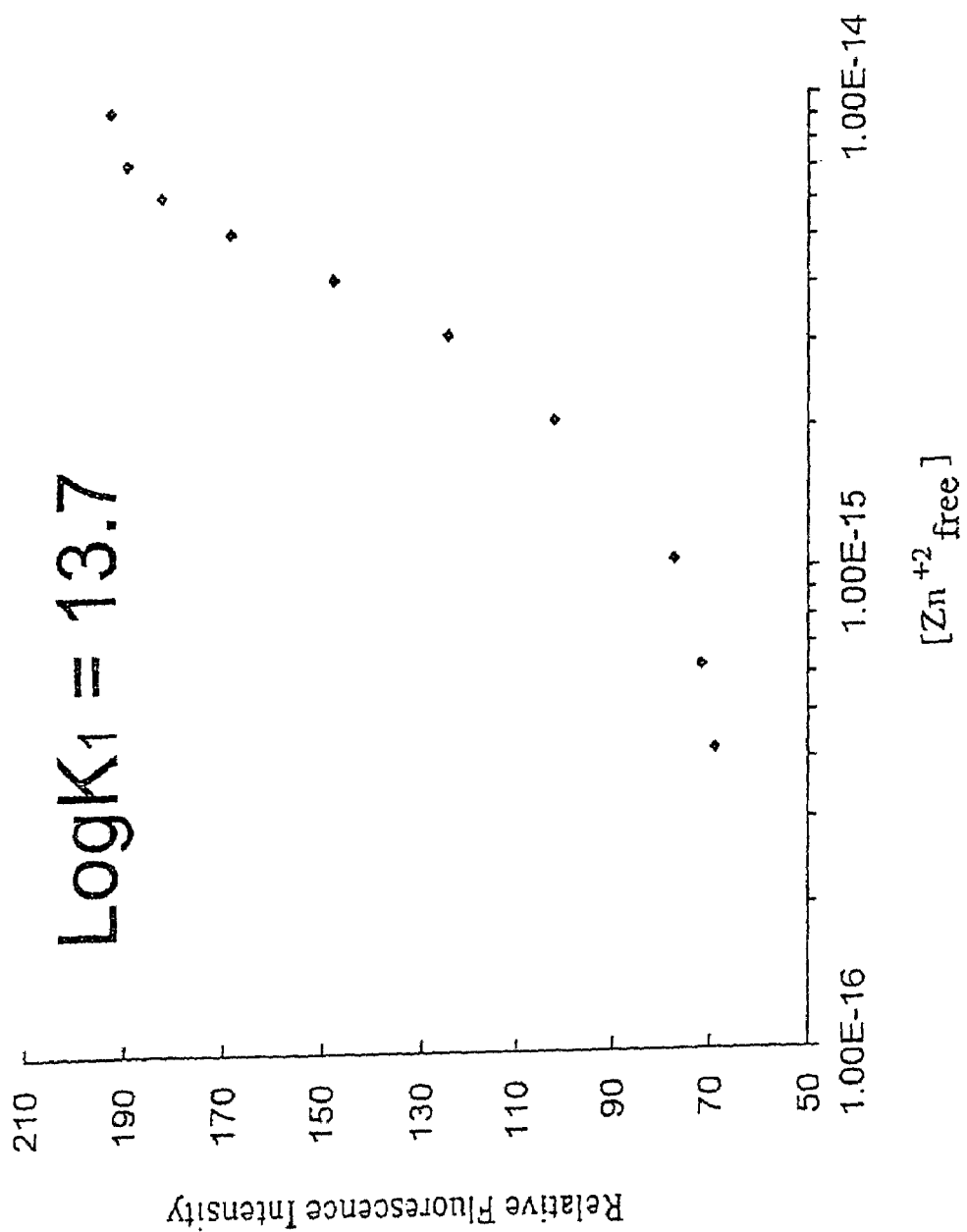
FIG. 12 illustrates TRS1 sensitivity to Zn(II).
Figure 13:
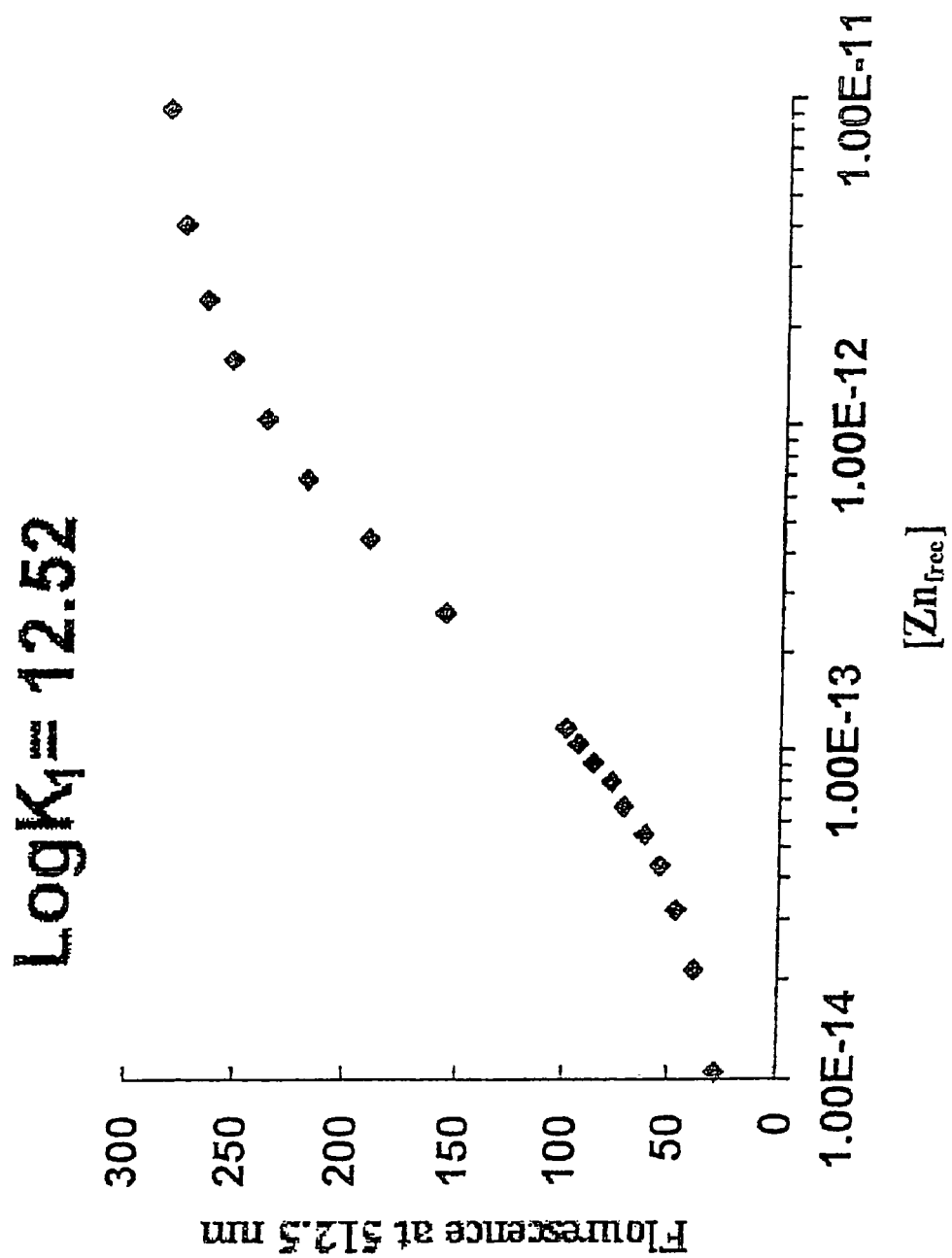
FIG. 13 illustrates TRS2 sensitivity to Zn(II).

FIGS. 12 and 13 show sensitivity of TRS 1 and TRS 2, respectively, for total Zn(II). In FIG. 12, the spectra shown are for total Zn(II) at 0, 2, 4, 6, 10, 20, 30, 40, 50, 60, 70, 80, 90 mM with corresponding free Zn(II) at $10^{-25.68}$, $10^{-15.38}$, $10^{-15.2}$, $10^{-14.98}$, $10^{-14.68}$, $10^{-14.5}$, $10^{-14.38}$, $10^{-14.2}$, $10^{-14.132}$, $10^{-14.07}$, and $10^{-14.02}$ M, respectively. In FIG. 13, the spectra shown are for total Zn(II) at 0.1, 0.2, 0.3, 0.4, 0.5, 0.6, 0.7, 0.8, 0.9, 1, 2, 3, 4, 5, 6, 7, 8, 9 M with corresponding free Zn(II) at $10^{-13.98}$, $10^{-13.67}$, $10^{-13.36}$, $10^{-13.26}$, $10^{-13.17}$, $10^{-13.1}$, $10^{-13.04}$, $10^{-12.98}$, $10^{-12.93}$, $10^{-12.58}$, $10^{-12.35}$, and $10^{-12.16}$, $10^{-11.98}$, $10^{-11.8}$, $10^{-11.62}$, $10^{-11.38}$, $10^{-11.03}$ M, respectively.

Figure 16:
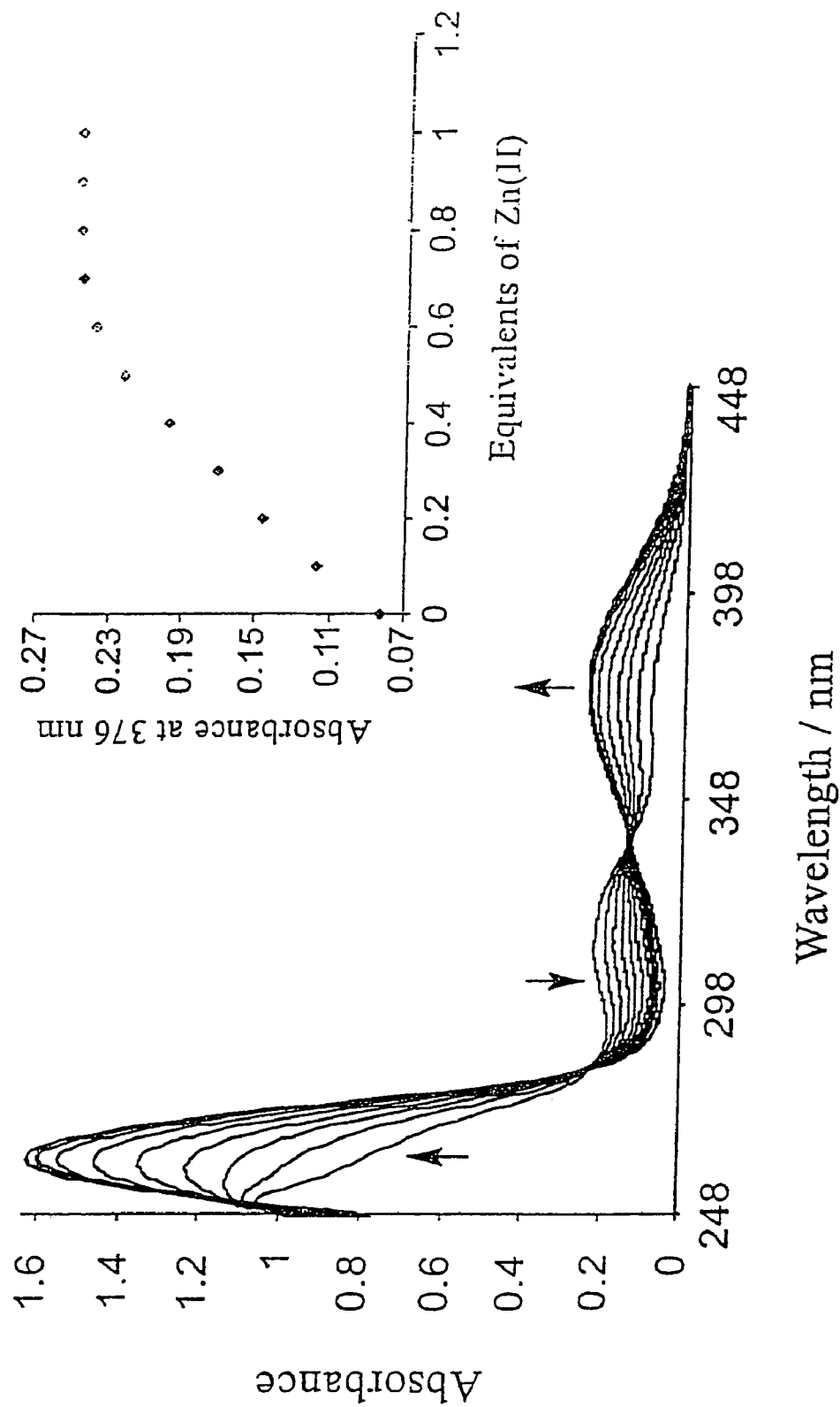
FIG. 16 shows UV-visible absorbance of TRS as a function of Zn(II) concentration.

FIG. 16 shows UV-visible absorbance of 30 micromolar TRS as a function of Zn(II) concentration. The spectra were acquired in 1% DMSO aqueous solution (0.1 M KNO3, 50 mM HEPES, pH 7.0). The inset is a molar ratio plot.

Figure 17:
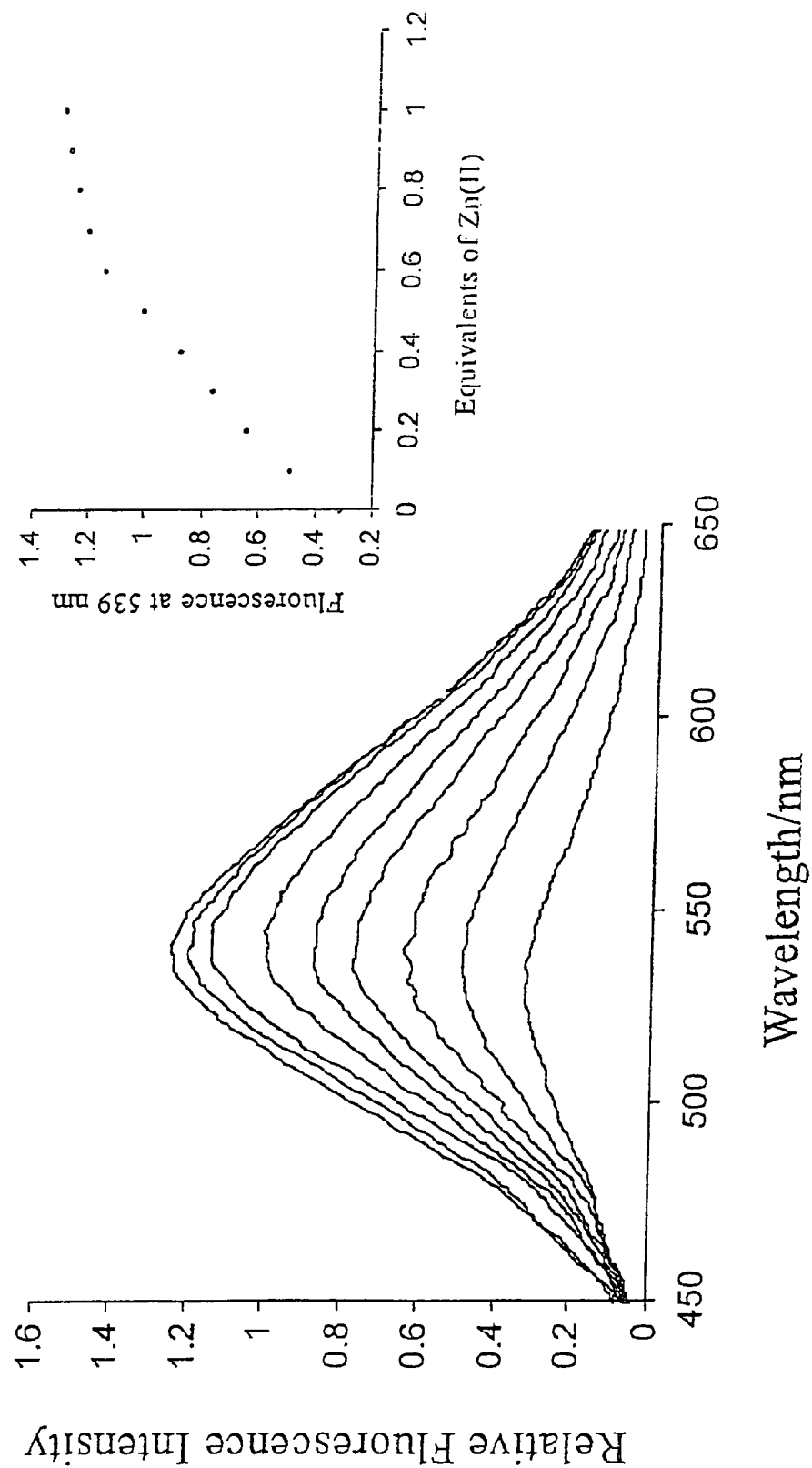
FIG. 17 shows fluorescence enhancement of TRS as a function of Zn(II) concentration.

FIG. 17 shows UV-visible absorbance of 30 micromolar TR as a function of Zn(II) concentration. The spectra were acquired in 20% DMSO aqueous solution (0.1 M KNO3, 50 mM HEPES, pH 7.0). The inset is a molar ratio plot.

Figure 18:
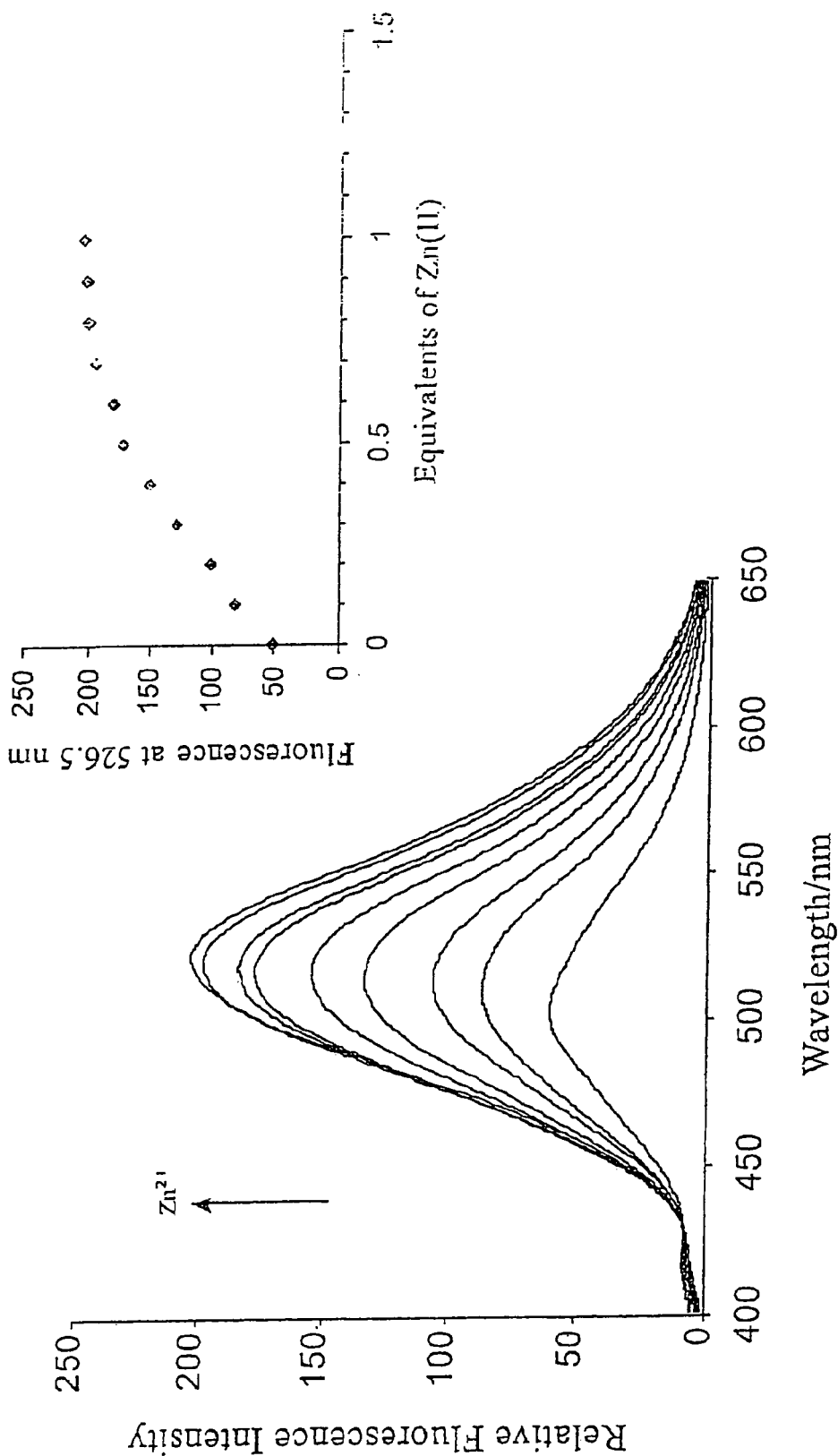
FIG. 18 shows fluorescence enhancement of TRS as a function of Zn(II) concentration.

FIG. 18 shows enhancement of 30 micromolar TRS fluorescence as a function of Zn(II) concentration. The spectra were acquired in 1% DMSO aqueous solution (0.1 M KNO3, 50 mM HEPES, pH 7.0). The inset is a molar ratio plot.

Figure 19:
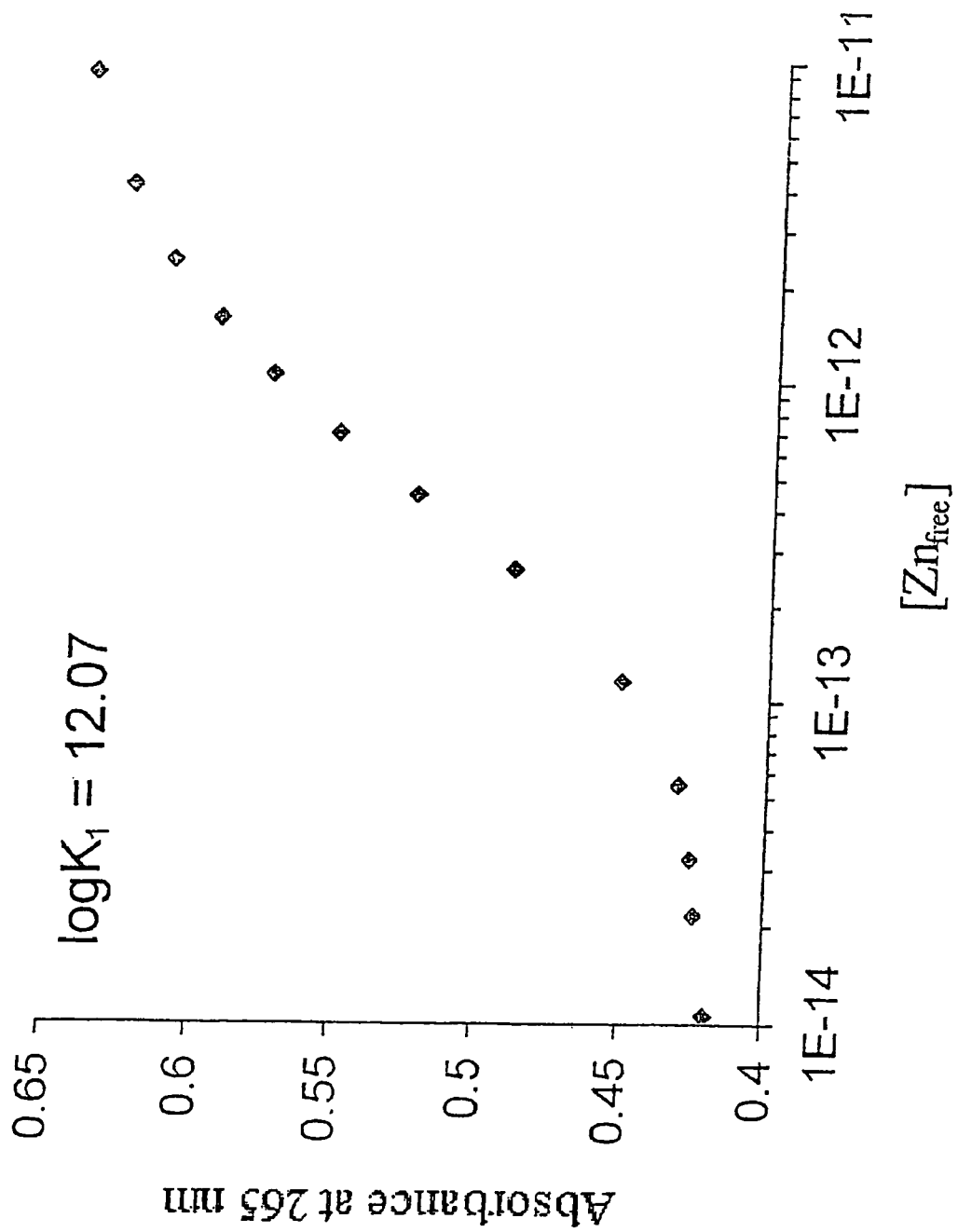
FIG. 19 shows fluorescence response of TRS to buffered Zn(II) solutions.
Figure 20:
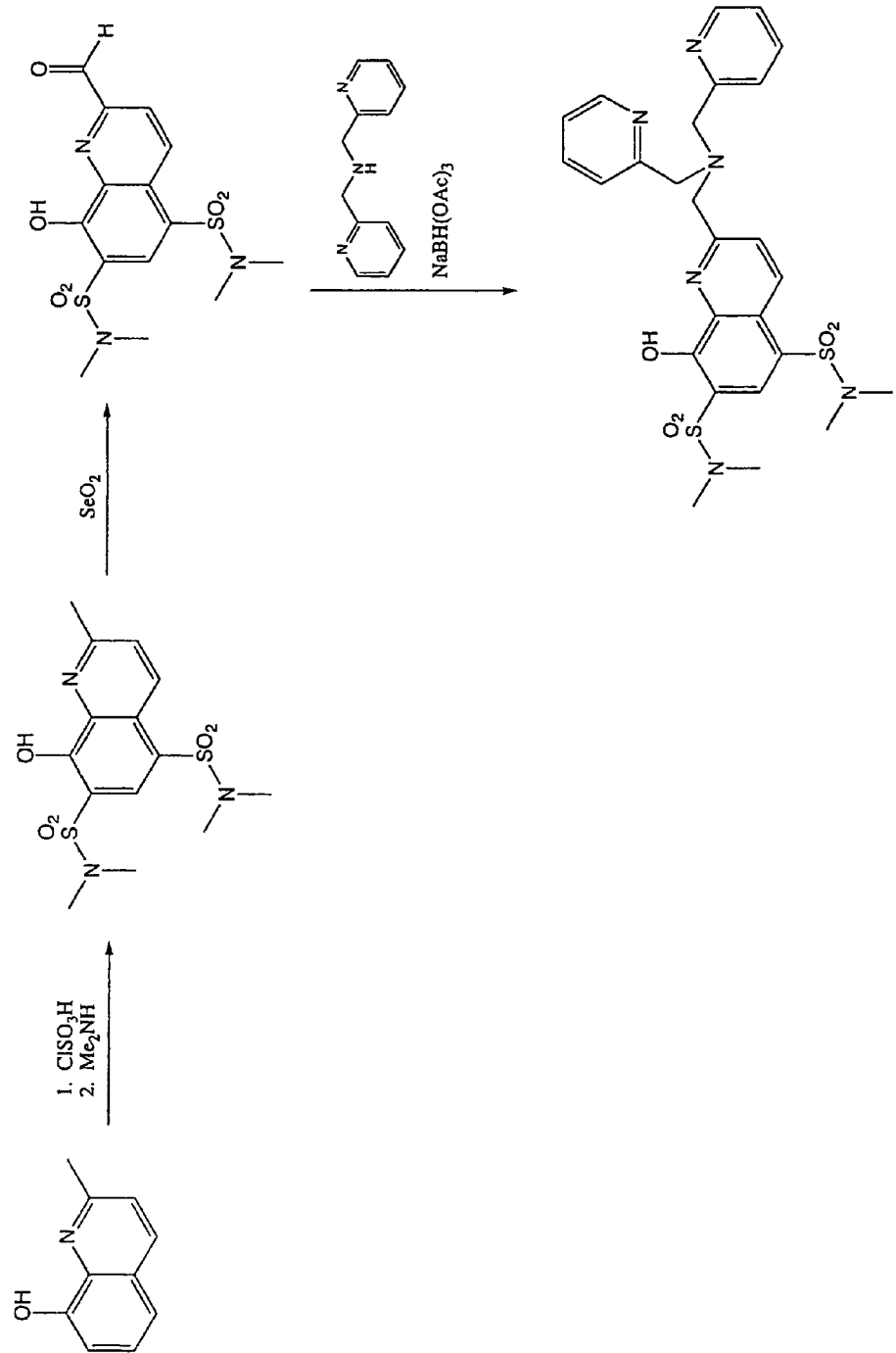
FIG. 20 shows synthesis of TRSS 2.

FIG. 19 shows enhancement of 30 micromolar TR fluorescence as a function of Zn(II) concentration. The spectra were acquired in 50% DMSO aqueous solution (0.1 M KNO3, 50 mM HEPES, pH 7.0). The inset is a molar ratio plot.

While use of the tripodal ligands for detecting Zn(II) or Cd(II) detection has been illustrated using florescence microscopy, other type of fluorescence detection are possible using these ligands. For example, Zn(II) or Cd(II) can be detected using the ligands of the present invention in conjunction with other fluorescent techniques such as spectroscopy or time-resolved fluorescence spectroscopy/microscopy.

It is to be understood that the phraseology or terminology employed herein is for the purpose of description and not of limitation. The means and materials for carrying out disclosed functions may take a variety of alternative forms without departing from the invention. Thus, the expressions "means to . . . " and "means for . . . " as may be found the specification above, and/or in the claims below, followed by a functional statement, are intended to define and cover whatever structural, physical, chemical, or electrical element or structures which may now or in the future exist for carrying out the recited function, whether or not precisely equivalent to the embodiment or embodiments disclosed in the specification above, and it is intended that such expressions be given their broadest interpretation.

What is claimed is:

1. A compound which is:

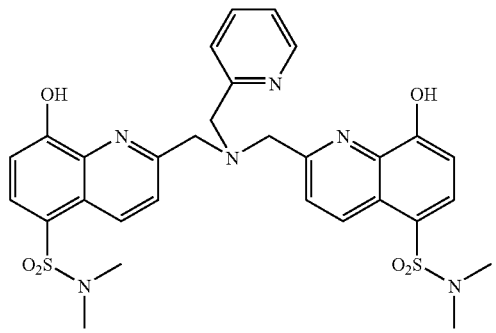

2. A compound which is:

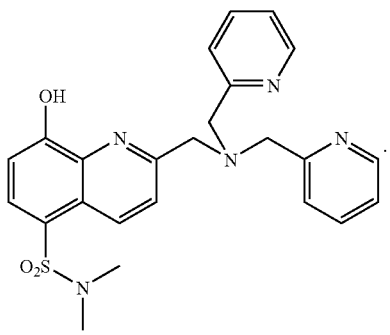

3. A compound which is:

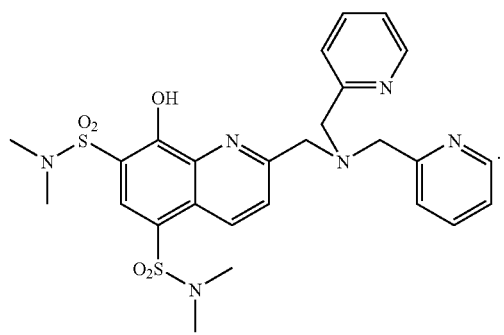

* * * * *